(12) United States Patent
Haupt

(10) Patent No.: US 10,898,258 B2
(45) Date of Patent: Jan. 26, 2021

(54) SURGICAL CAUTERIZER WITH SMOKE EVACUATION PORTS AND A CENTRAL VACUUM

(71) Applicant: Russell Scott Haupt, Murray, UT (US)

(72) Inventor: Russell Scott Haupt, Murray, UT (US)

( * ) Notice: Subject to any disclaimer, the term of this patent is extended or adjusted under 35 U.S.C. 154(b) by 849 days.

(21) Appl. No.: 15/147,581

(22) Filed: May 5, 2016

(65) Prior Publication Data

US 2017/0319264 A1 Nov. 9, 2017

(51) Int. Cl.
*A61B 18/14* (2006.01)
*A61B 18/00* (2006.01)
*A61B 17/29* (2006.01)

(52) U.S. Cl.
CPC .. *A61B 18/1442* (2013.01); *A61B 2017/2926* (2013.01); *A61B 2018/00595* (2013.01); *A61B 2018/00958* (2013.01); *A61B 2018/1462* (2013.01); *A61B 2018/1467* (2013.01); *A61B 2018/1495* (2013.01); *A61B 2218/008* (2013.01)

(58) Field of Classification Search
CPC .. A61B 2218/006–008; A61B 18/1442; A61B 2018/1467; A61B 2018/00958; A61B 2018/00595
See application file for complete search history.

(56) References Cited

U.S. PATENT DOCUMENTS

| 4,096,864 | A | * | 6/1978 | Kletschka | A61B 17/30 |
| | | | | | 604/35 |
| 5,902,301 | A | * | 5/1999 | Olig | A61B 18/1442 |
| | | | | | 606/48 |
| 6,050,996 | A | * | 4/2000 | Schmaltz | A61B 18/14 |
| | | | | | 606/50 |
| 6,142,995 | A | * | 11/2000 | Cosmescu | A61B 18/042 |
| | | | | | 604/34 |
| 6,926,717 | B1 | * | 8/2005 | Garito | A61B 18/1442 |
| | | | | | 606/51 |
| 9,289,261 | B2 | | 3/2016 | Shvetsov et al. | |
| 9,375,253 | B2 | | 6/2016 | Greep et al. | |
| 2003/0181909 | A1 | * | 9/2003 | Kirwan, Jr. | A61B 18/1442 |
| | | | | | 606/51 |
| 2004/0254573 | A1 | * | 12/2004 | Dycus | A61B 18/00 |
| | | | | | 606/51 |
| 2007/0129722 | A1 | * | 6/2007 | Cosmescu | A61M 39/1055 |
| | | | | | 606/42 |

(Continued)

*Primary Examiner* — Jaymi E Della
*Assistant Examiner* — Sean W Collins
(74) *Attorney, Agent, or Firm* — Thorpe North & Western, LLP

(57) ABSTRACT

A surgical cauterizer includes an elongate body member having a tapered distal-end portion terminating at an apex. A cauterizing tip extends from the apex. A hollow passageway is formed in the interior of the elongate body member. Formed in the tapered distal-end portion of the elongate body member is at least one smoke intake port for providing a smoke evacuation pathway between a region proximate the cauterizing tip and the hollow passageway within the elongate body member. A tube connected to an outlet of the hollow passageway may provide a vacuum for evacuating the smoke generated by cauterization. In an embodiment, the elongate body member may include a first and second arms that define a forceps operable between an open position and a closed position.

7 Claims, 8 Drawing Sheets

(56) References Cited

U.S. PATENT DOCUMENTS

| | | | |
|---|---|---|---|
| 2014/0276795 A1* | 9/2014 | Batchelor | A61B 18/1233 606/42 |
| 2015/0080879 A1* | 3/2015 | Trees | A61B 18/1445 606/40 |
| 2015/0282871 A1* | 10/2015 | Wang | A61B 18/1442 606/52 |
| 2016/0157918 A1 | 6/2016 | Shvetsov et al. | |

* cited by examiner

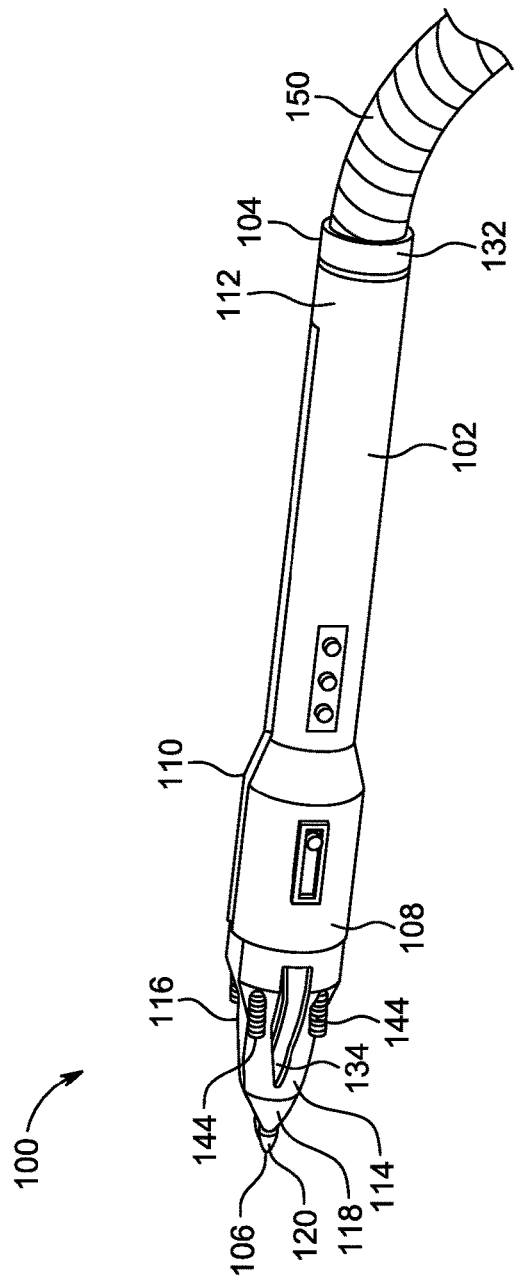
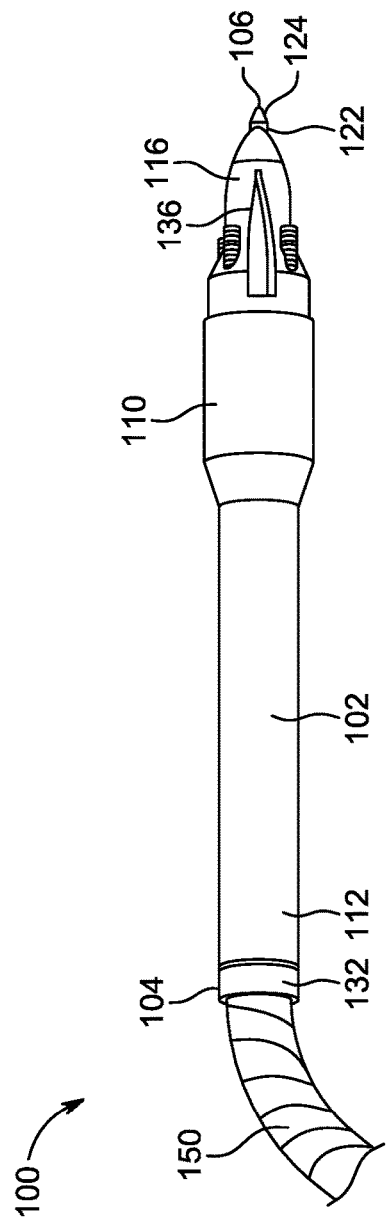
FIG. 1
FIG. 2

US 10,898,258 B2

SURGICAL CAUTERIZER WITH SMOKE EVACUATION PORTS AND A CENTRAL VACUUM

CROSS-REFERENCE TO RELATED APPLICATIONS

None.

STATEMENT REGARDING FEDERALLY SPONSORED RESEARCH OR DEVELOPMENT

Not Applicable.

BACKGROUND OF THE INVENTION

1. The Field of the Invention

The present invention relates generally to medicine and veterinary medicine, more specifically to surgery, and is particularly concerned with electrosurgical instruments.

2. Description of Related Art

Electrocautery and electrosurgery are surgical procedures that utilize hand-held tools that are connected to a power source. However, even though both of these procedures are applied within several medical specialties, they are typically quite different in terms of both tools used and method of application. Each of these is explained in more detail below.

Electrocautery, sometimes referred to as thermal cautery, may use an electrical current to heat a resistant metal electrode. The hot electrode is then placed directly onto the treatment area destroying that specific tissue. In electrocautery, the current does not pass through the patient; thus, the procedure can be safely used in patients with implanted electrical devices such as cardiac pacemakers, implantable cardioverter-defibrillators, and deep-brain stimulators.

In contrast, electrosurgery is a group of commonly used procedures that utilize the passage of high-frequency alternating electrical current through living tissue to accomplish a desired result. The electricity used is a form of alternating current similar to that used to generate radio waves. The typical frequency is quite high, with the norm being around 200,000 to 500,000 cycles per second. This ensures that the current passes through the patient's tissue as opposed to producing an electric shock effect. The resistance of the tissue at the tip with the electrical current creates heat that performs the desired result.

Electrosurgery can be performed using either monopolar or bipolar-energy in conjunction with a specialized instrument. In monopolar electrosurgery, a current passes from the probe electrode, to the tissue and through the patient to a return pad to complete the electric current circuit. Monopolar electrosurgery can be used for several modalities including cut, blend, desiccation, and fulguration. Monopolar electrosurgery is commonly used because of its versatility and effectiveness. Monopolar electrosurgery may utilize either a single tip in a standard configuration or a forceps type cauterizer.

In bipolar electrosurgery, the electrical current only passes through the tissue held between the two arms of a forceps shaped electrode. Bipolar electrosurgery uses lower voltages than monopolar so less energy is required. But, because it has limited ability to cut and coagulate large bleeding areas, it is more ideally used for those procedures where tissues can be easily grabbed on both sides by the forceps electrode. Electrosurgical current in the patient is restricted to just the tissue between the tips of the forceps electrode. This gives better control over the area being targeted, and helps prevent damage to other sensitive tissues. With bipolar electrocautery, the risk of patient burns is reduced significantly.

Recently, concern has been raised regarding the toxicity of the surgical smoke generated by cauterization procedures. This smoke has been found to contain chemicals that, through inhalation, may harm patients or medical personnel. While surgical smoke containing potentially carcinogenic and irritant chemicals is an inevitable consequence of cauterization, improvements are needed in order to reduce the potential harm to patients and medical personnel.

The features and advantages of the invention will be set forth in the description which follows, and in part will be apparent from the description, or may be learned by the practice of the invention without undue experimentation. The features and advantages of the invention may be realized and obtained by means of the instruments and combinations particularly pointed out in the appended claims.

BRIEF DESCRIPTION OF THE DRAWINGS

The features and advantages of the disclosure will become apparent from a consideration of the subsequent detailed description presented in connection with the accompanying drawings in which:

FIG. 1 is a perspective view of a surgical cauterization tool according to an embodiment of the present disclosure;

FIG. 2 is a side view of the surgical cauterization tool according to an embodiment of the present disclosure;

DETAILED DESCRIPTION

Figure 3:
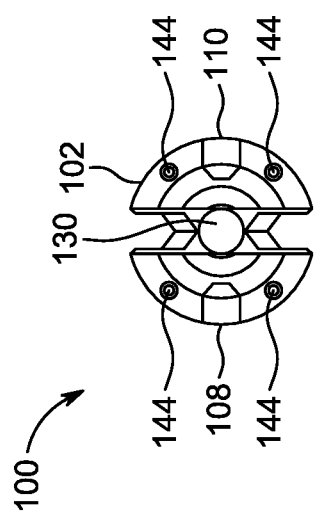
FIG. 3 is an end view of the surgical cauterization tool according to an embodiment of the present disclosure.

For the purposes of promoting an understanding of the principles in accordance with the disclosure, reference will now be made to the embodiments illustrated in the drawings and specific language will be used to describe the same. It will nevertheless be understood that no limitation of the scope of the disclosure is thereby intended. Any alterations and further modifications of the inventive features illustrated herein, and any additional applications of the principles of the disclosure as illustrated herein, which would normally occur to one skilled in the relevant art and having possession of this disclosure, are to be considered within the scope of the disclosure claimed.

In describing and claiming the present disclosure, the following terminology will be used in accordance with the definitions set out below. As used in this specification and the appended claims, the singular forms "a," "an," and "the" include plural referents unless the context clearly dictates otherwise. As used herein, the terms "comprising," "including," "containing," "characterized by," "having," and grammatical equivalents thereof are inclusive or open-ended terms that do not exclude additional, unrecited elements or method steps. As used herein, the term "proximal" shall refer broadly to the concept of a nearest portion. As used herein, the term "distal" shall generally refer to the opposite of proximal, and thus to the concept of a further portion, or a furthest portion, depending upon the context.

It is an objective of the present invention to provide an effective surgical cautery system with a smoke evacuation feature to evacuate and filter surgical smoke from a surgical site during a procedure.

It is an objective of the present invention to provide an effective surgical cautery system with a smoke evacuation feature that allows for monopolar cautery and bipolar cautery.

It is an objective of the present invention to provide an effective surgical cautery system with a central smoke evacuation feature that allows for monopolar cautery and bipolar cautery.

It is an objective of the present invention to provide a hand-held cautery device that includes one or more smoke evacuation ports proximate a cauterizing tip. In an embodiment, the device is connected to a standard suction or surgical smoke evacuator that generates a vacuum that is able to suction surgical smoke from a region proximate the cauterizing tip during a surgical procedure.

It is an objective of the present invention to provide a hand-held cautery device that includes a hollow passageway extending between an outlet and one or more smoke evacuation ports formed proximate a distal end of the device. In an embodiment, the outlet includes a connector for attaching a tube that is connected to a surgical smoke evacuator.

It is an objective of the present invention to provide a hand-held cautery device that includes a hollow passageway extending between an outlet and one or more smoke evacuation ports formed in a tapered-distal end of the device.

It is further an object of the present invention to provide a hand-held cautery device that comprises a base connected to each of a first arm and a second arm, the base joining the first and second arms at their proximal base ends so as to form a forceps manipulable by a user between an open position and a closed position, where each of the first and second arms comprises an inner surface that forms a hollow passageway when the forceps are manipulated to the closed position by a user.

It is further an object of the present invention to provide a hand-held cautery device that comprises an elongate body member having a tapered distal-end portion with a cauterizing tip, where at least one smoke intake port is formed in the tapered distal-end portion of the elongate body member, the at least one smoke intake port providing a smoke evacuation pathway between a region proximate the cauterizing tip and the hollow passageway within the elongate body member.

It is further an object of the present invention to provide a hand-held cautery device that has multiple modes of operation, including as a monopolar cauterizer and a bipolar cauterizer.

It is further an object of the present invention to provide a hand-held cautery device that has multiple modes of operation, including selectable blends of the standard cut mode and coagulation mode.

It is further an object of the present invention to provide a hand-held cautery device that has multiple modes of operation, including as a thermal cauterizer, a monopolar cauterizer, or a bipolar cauterizer, where a user can switch between the different modes of operation using controls located on the hand-held cautery device.

It is further an object of the present invention to provide a hand-held cautery device that is connected to a smoke evacuation tube by a swivel or a jointed connection such that the device and the tube may move relatively independent of each other.

It is further an object of the present invention to provide a hand-held cautery device that comprises a base connected to each of a first arm and a second arm, the base joining the first and second arms at their proximal base ends so as to form a forceps manipulable by a user between an open position and a closed position, the device further comprising a locking feature for locking the forceps in the closed position.

It is further an object of the present invention to provide a hand-held cautery device that comprises a base connected to each of a first arm and a second arm, the base joining the first and second arms at their proximal base ends so as to form a forceps manipulable by a user between an open position and a closed position, the device selectively operable as one of a monopolar cautery and as a bipolar cautery.

It is further an object of the present invention to provide a hand-held cautery device that comprises a base connected to each of a first arm and a second arm, the base joining the first and second arms at their proximal base ends so as to form a forceps manipulable by a user between an open position and a closed position, the first arm and the second arm having an inner C-shaped concave surface that together form a hollow passageway when the forceps are manipulable to the closed position.

It is further an object of the present invention to provide a hand-held cautery device that comprises a base connected to each of a first arm and a second arm, the base joining the first and second arms at their proximal base ends so as to form a forceps manipulable by a user between an open position and a closed position, the device comprising a hollow passageway for evacuating surgical smoke generated during cauterization.

It is further an object of the present invention to provide a hand-held cautery device that comprises interchangeable cauterizing tips.

It is further an object of the present invention to provide a hand-held cautery device that comprises one or more LED lights for illuminating a surgical site.

It is further an object of the present invention to provide a hand-held cautery device that comprises an internal hollow passageway for smoke evacuation, where the passageway has an improved cross sectional area to provide a stronger vacuum pressure near the cautery tip.

It is further an object of the present invention to provide a hand-held cautery device that is adaptable to the style of cautery for the surgeon.

It is further an object of the present invention to provide a hand-held cautery device that includes interchangeable cautery tips to adapt to different modes of operation.

It is further an object of the present invention to provide a base unit for use with a hand-held cauterizing device, where the base unit includes a surgical smoke evacuator that generates a vacuum that is able to suction surgical smoke.

It is further an object of the present invention to provide a hand-held cautery device that includes a plurality of smoke evacuation ports proximate the cauterizing tip for improved smoke evacuation.

Referring now to FIGS. 1, 2, 4 and 5, there is shown a hand-held surgical cauterizing device 100 according to an embodiment of the present disclosure. The device 100 comprises an elongate body member 102 that extends along a longitudinal axis from a proximal end 104 to a distal end 106. As perhaps best observed in FIGS. 4 and 5, but visible in FIGS. 1 and 2 as well, the body member 102 comprises a first arm 108 and a second arm 110. The first arm 108 and the second arm 110 extend from a common base portion 112 on the body member 102 to thereby define forceps. That is, the first arm 108 and the second arm 110 are joined at their proximal base ends so as to form a forceps manipulable by a user between an open position (FIG. 4) and a closed position (FIG. 5) as will be explained in more detail hereinafter. It will be appreciated that the forceps may be naturally biased in the open position as observed in FIG. 4.

Figure 4:
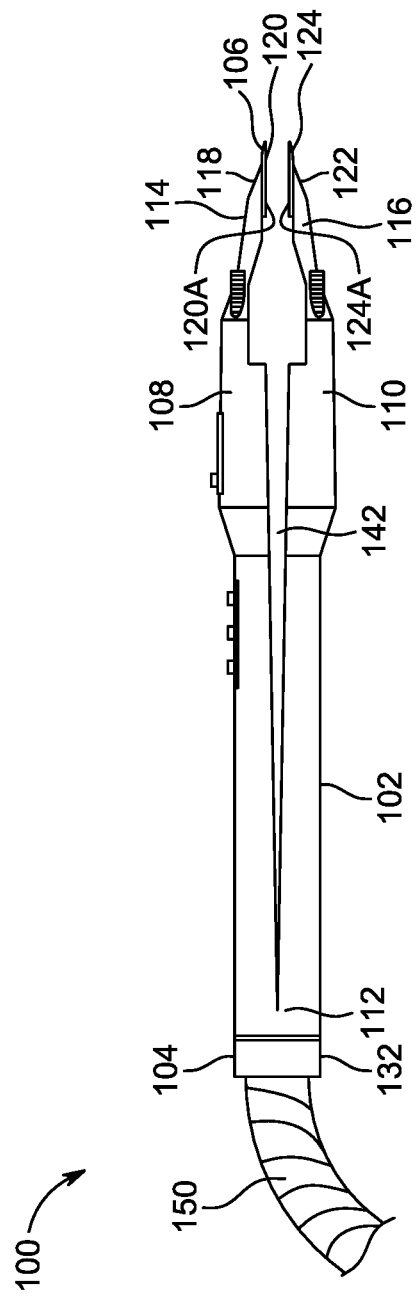
FIG. 4 is a side view of the surgical cauterization tool according to an embodiment of the present disclosure with the forceps feature in an open configuration.

In an embodiment, the first arm 108 comprises a tapered distal-end portion 114 that terminates at an apex 118. Extending from the apex 118 is a cauterizing tip 120. Similarly, the second arm 110 comprises a tapered distal-end portion 116 that terminates at an apex 122. Extending from the apex 122 is a cauterizing tip 124. It will be appreciated that an inner surface 120A of the tip 120 and an inner surface 124A of the tip 124 may be substantially flat as shown in FIG. 4.

Figure 5:
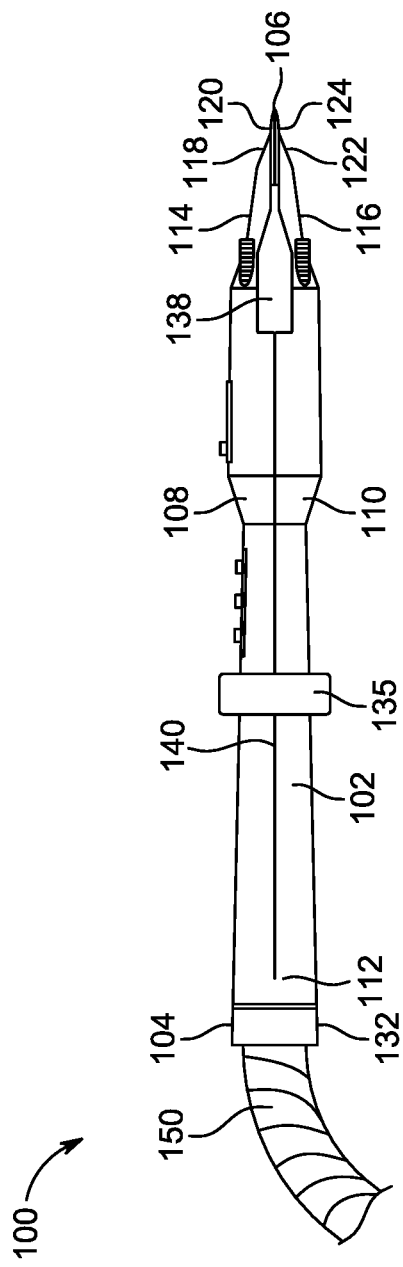
FIG. 5 is a side view of the surgical cauterization tool according to an embodiment of the present disclosure with the forceps feature in a closed configuration.

Referring now to FIG. 3, where like reference numerals depict the same components, extending along the length of the interior of the elongate body member 102 is a hollow passageway 130. It will be appreciated that the hollow passageway 130 forms a smoke evacuation pathway through the elongate body member 102. In particular, each of the arms 108 and 110 may comprise a generally C-shaped or U-shaped, concave inner surface such that a cross section of the hollow passageway 130 is circular when the forceps are operated to the closed position as shown in FIG. 5.

As observed in FIGS. 1, 2, 4, and 5, the passageway 130 is fluidly connected to a tube 150 attached to the proximal end 104 of the elongate body member 102 by a connector 132. In an embodiment, the connector 132 is a swivel connector or a jointed connector that allows the tube 150 and the elongate body member 102 to move relatively independently of each other. It will be appreciated that this type of connection allows a user to more freely manipulate the device 100 during a surgical procedure. In an embodiment, the tube 150 is removably attachable to the connector 132.

In this regard, the end of the tube 150 (not shown) may comprise a coupler for connecting to the connector 132. In an embodiment, the tube 150 may engage the connector 132 using a twist lock mechanism or a snap fit connection. It will be appreciated that the tube 150 may be attached to the body member 102 in any number of ways, all of which fall within the scope of the present disclosure.

As can be observed in FIGS. 1 and 2, formed in the tapered distal-end portion 114 of the first arm 108 is a smoke intake port 134 and formed in the tapered distal-end portion 116 of the second arm 110 is a smoke intake port 136. It will be appreciated that the smoke intake ports 134 and 136 form a fluid communication path between a region proximate the cauterizing tips and the hollow passageway 130 within the elongate body member 102. Further, as observed in FIG. 5, when the forceps are manipulated to the closed position, i.e., the first arm 108 and the second arm 110 held together, smoke intake ports 138 are formed between the tapered distal-end portion 114 of the first arm 108 and the tapered distal-end portion 116 of the second arm 110.

In addition, when the forceps are manipulated to the closed position, the gap between the first arm 108 and the second arm 110 is closed and is substantially sealed along the seam 140 as shown in FIG. 5. It will be appreciated that the substantially sealed seam 140 prevents smoke from escaping the hollow passageway 130 extending through the body member 102. In this regard, the hollow passageway 130 may not be fully formed until the forceps are manipulated to the closed position. In particular, as observed in FIGS. 4 and 7, there exists a gap 142 between the first arm 108 and the second arm 110 while the forceps are in the open position.

Figure 6:
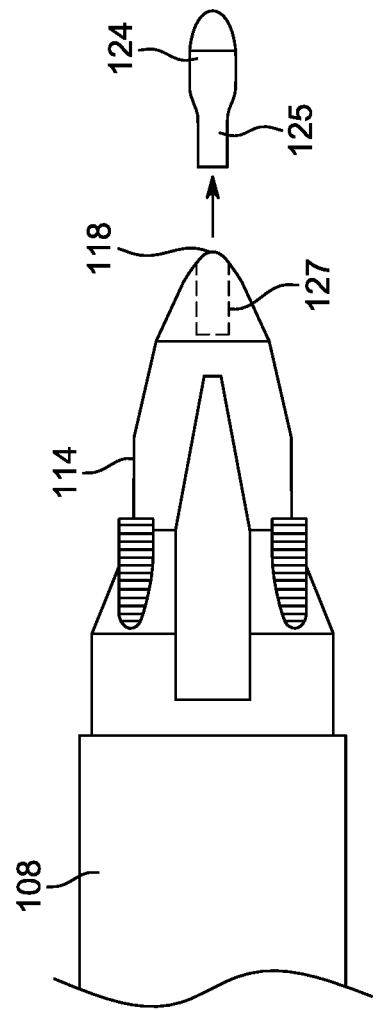
FIG. 6 is a fragmentary view of the distal-end portion of the surgical cauterization tool and showing the removable cauterization tip.
Figure 9:
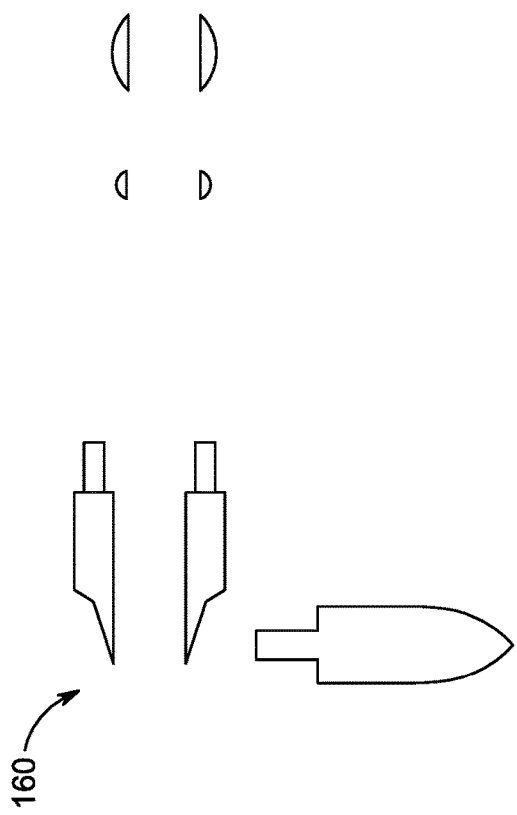
FIG. 9 depicts a set of replacement cauterizing tips.

Referring now to FIG. 6, as can be observed, the cauterizing tip 124 is removable from the apex 118 of the tapered distal-end portion 114 of the first arm 108. In this regard, the tip 124 may include a prong 125 that is configured and adapted to slide into a slot 127 formed in the apex 118. It will be appreciated that the prong 125 may come into contact with an electrical connector (not shown) inside of the slot 127 in order to provide electrical power to the tip 124. It will be appreciated that the use of interchangeable tips may allow a user to select tips of different shapes and sizes depending on the surgical procedure to be performed. In addition, the use of interchangeable tips may allow the device 100 to be used in different operating modes, including as a thermal cauterizer, a monopolar cauterizer, or a bipolar cauterizer. Likewise, the tip 124 is also removable from the apex 122 of the second arm 110 in a similar manner. Referring to FIG. 9, there is depicted a set of interchangeable tips 160 that may be utilized with the device 100. It will be appreciated that the working end of the tips 160 may have different shapes. For example, some of the tips 160 may have a fine or sharp working ends for better cutting while others may be thicker for coagulation. In this regard, the fine or sharp working end has a high current density due to the small "active" area at the very end of the tip.

As can be seen on FIGS. 1 and 3, disposed on the first arm 108 and the second arm 110 are a plurality of LED lights 144. It will be appreciated that the lights 144 may provide improved illumination of a surgical site on a patient. In an embodiment, the device 100 comprises four LED lights 144. In other embodiments, the device 100 may comprise one or more LED lights 144.

Figure 7:
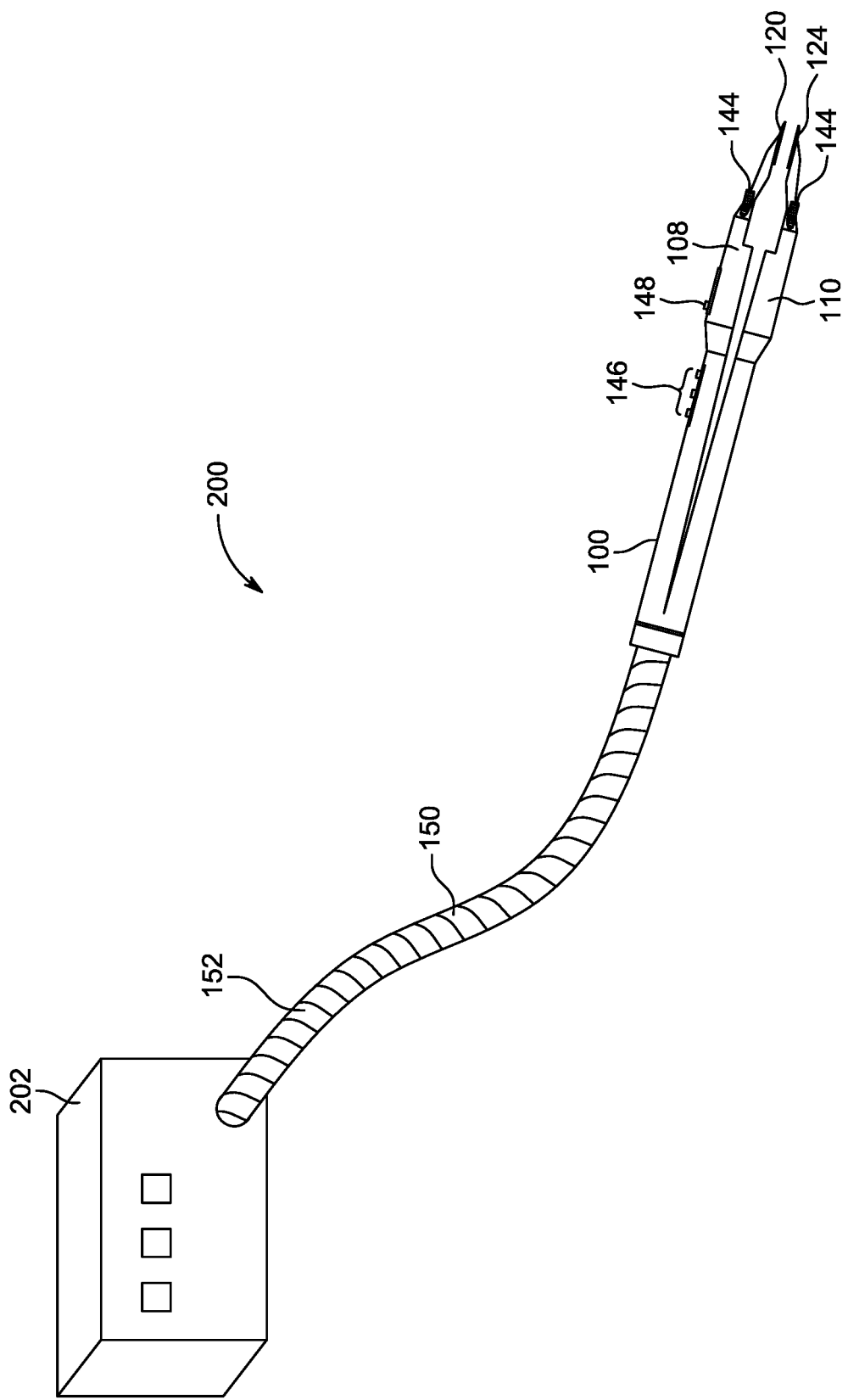
FIG. 7 depicts a surgical cauterization system according to an embodiment of the present disclosure.
Figure 8:
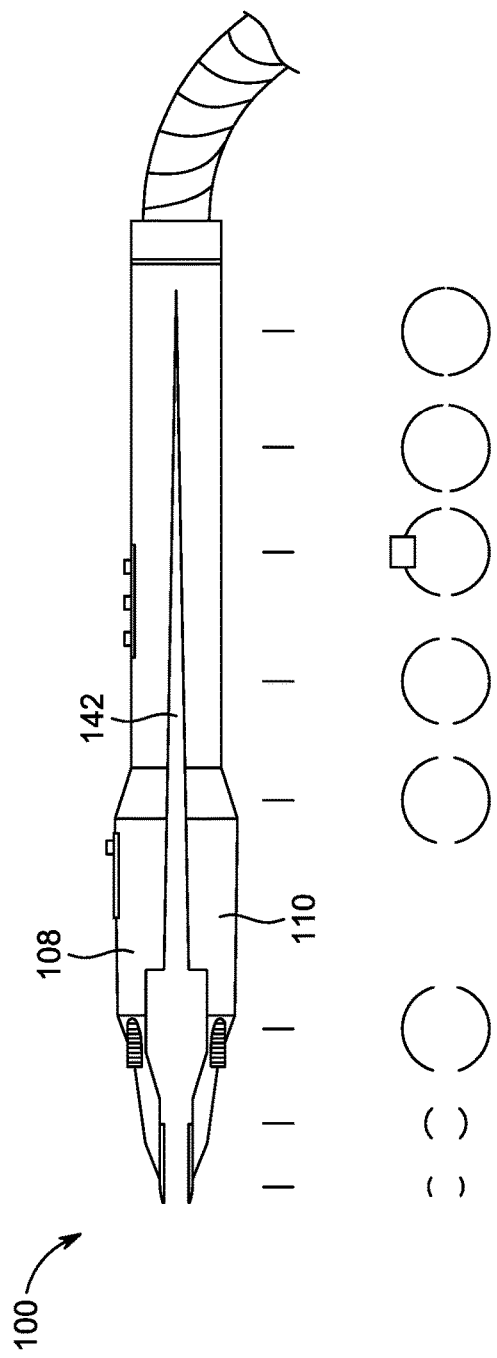
FIG. 8 is a side view of the surgical cauterizer and its corresponding cross-sectional views along its longitudinal axis.

Referring now to FIG. 7, where like reference numerals depict the same components, there is depicted a cauterization system 200 according to an embodiment of the present disclosure. The system 200 comprises a multifunction base unit 202 connected to the device 100. Extending between the unit 202 and the device 100 is the tube 150. That is, the tube 150 is connected at one end to the unit 202 and the other end is connected to the device 100. Incorporated into the tube 150 may be wires 152.

In an embodiment, the unit 202 comprises a power generator for providing power to the device 100 through the wires 152. In this regard, the generator of the unit 202 may generate and supply different modes of power such that the device 100 may operate in one of a thermal cauterizer mode, a monopolar cauterizer mode, and a bipolar cauterizer mode. The modes of operation of the generator may be controlled directly from the device 100 through buttons 146. In this regard, the wires 152 may include at least one wire for sending a control signal between the device 100 and the unit 202. In addition, the device 100 includes an on/off switch 148 for energizing and de-energizing the tips 120 and 124. The buttons 146 may further be utilized to control the LED lights 144. In an embodiment, the buttons 146 may switch the device 100 into different electrosurgery modes, including cut, blend cut, and coagulation. The power level may be variable by a user between discrete levels using the buttons 146. For example, the electrosurgical modes may be variable as shown in Table 1 below:

TABLE 1

| Cut | Coagulation |
| --- | --- |
| 100% | 0% |
| 70% | 30% |
| 50% | 50% |
| 30% | 70% |
| 0% | 100% |

The unit 202 may further include a surgical smoke evacuator that generates a vacuum that is able to suction surgical smoke from a region proximate the tips 120 and 124, through the smoke intake ports 134, 136, and 138, into the hollow passageway 130, through the tube 150, and then into the unit 202. In this regard, the unit 202 may include a filter (not shown) for filtering the surgical smoke. The operation of the surgical smoke evacuator may be controlled from the buttons 146 on the device 100 that are operable to transmit control signals to the unit 202 through wires 152. It will be appreciated that the surgical smoke evacuator and the power generator may be part of a single unit as shown in FIG. 7 or two separate units.

Each of the modes of operation of the system 202 will now be explained in more detail. In the thermal cauterizer mode, one or both of the tips 120 and 124 is heated by a direct or alternating current provided by the unit 202. The heated tip or tips 120 and 124 are then applied to living tissue to achieve the desired results. In the thermal cauterizer mode, the forceps feature of the device 100 may be held or locked in a closed position as shown in FIG. 5.

In the monopolar cauterizer mode, electrical current travels from one or both of the tips 120 and 124 through the patient until it reaches a return electrode (not shown) placed in proximity on the patient's skin, most typically on the opposite side of the body from the incision and then the energy returns to the generator in the unit 202. In the monopolar cauterizer mode, the forceps feature of the device 100 may be held or locked in a closed position as shown in FIG. 5. In this regard, the device 100 may include a locking feature such as a ring 135 that slides up the elongate body member 102 to hold the first arm 108 and the second arm 110 in the closed position as shown in FIG. 5. In an embodiment, the locking feature may include one of a clip, a snap lock, hook and catch, and a resilient member. In another embodiment, the forceps feature of the device 100 may be utilized in the monopolar cauterizer mode.

In the bipolar cauterizer mode, current in the patient is restricted to just the tissue held between the tips 120 and 124. Because the path of the electrical current is confined to the tissue between the two tips 120 and 124, it can be used on patients with implanted electronic devices to prevent electrical current passing through the device causing a short-circuit or misfire.

In an embodiment, the tube 150 may comprise a six to eight foot length of light weight plastic hollow tubing, but strong enough to be sterilized or disposable with electrical wires circling the outer surface. The end of the electrical wires may terminate in a plug that matably engages with a corresponding plug on the device 100.

Figure 10:
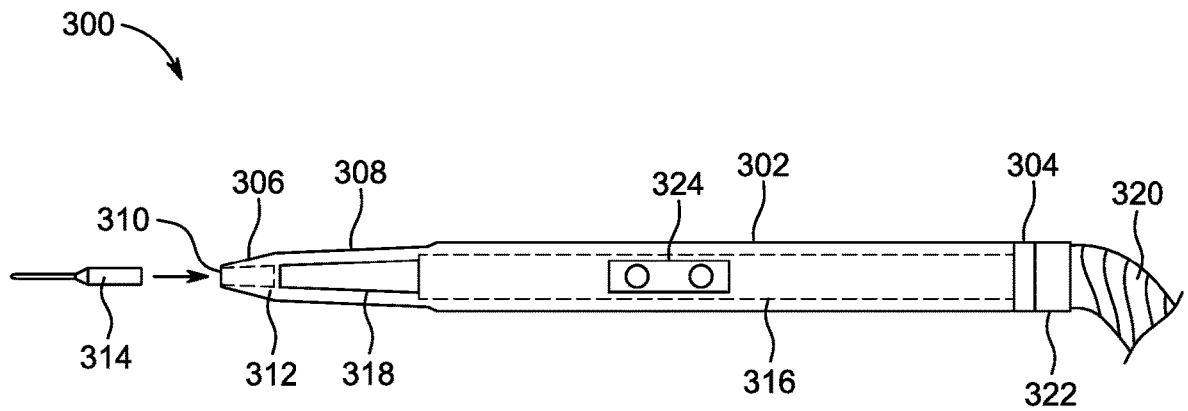
FIG. 10 depicts a side view of a surgical cauterization tool according to an embodiment of the present disclosure.

Referring to FIG. 10, there is depicted a hand-held surgical cauterizing device 300 according to an embodiment of the present disclosure. The device 300 may comprise an elongate body member 302. The elongate body member 302 may extend from a proximal end 304 to a distal end 306. The distal end 306 may be preceded by a tapered-distal end portion 308. The tapered-distal end portion 308 may taper in the proximal-to-distal direction and terminate at an apex 310.

Formed in the apex 310 may be a slot 312 (shown in dashed lines) configured and adapted for receiving a removable cauterizing tip 314. It will be appreciated that the cauterizing tip 314 may be interchangeable with other tips with different operating characteristics. For example, different parts of a surgical procedure may require different tips.

Formed in the interior of the elongate body member 302 is a hollow passageway 316 (shown in dashed lines) that extends from an outlet in the proximal end 304 to the tapered-distal end portion 308. The passageway 316 may be formed by an inner sidewall of the body member 302 or a tubular member. Formed in the tapered-distal end portion 308 may be at least one smoke intake port 318 that forms a smoke evacuation pathway from an area proximate the tip 314 and into the hollow passageway 316. The outlet of the passageway 316 may be connected to a tube 320 by a connector 322. Electrical leads for powering the tip 314 may be incorporated into the tube 320 or may be separate. In an embodiment, the connector 322 is one of a swivel connector or jointed connector. The tube 320 may be connected to an external suction generation device (not shown) to generate vacuum for removing surgical smoke proximate the tip 314.

User controls 324 on the elongate body member 302 may allow a user to energize and de-energize the tip 314. In addition, user controls 324 may allow a user to vary the blend or power to the tip 314. In an embodiment, the device 300 is a monopolar cauterizer.

Figure 11:
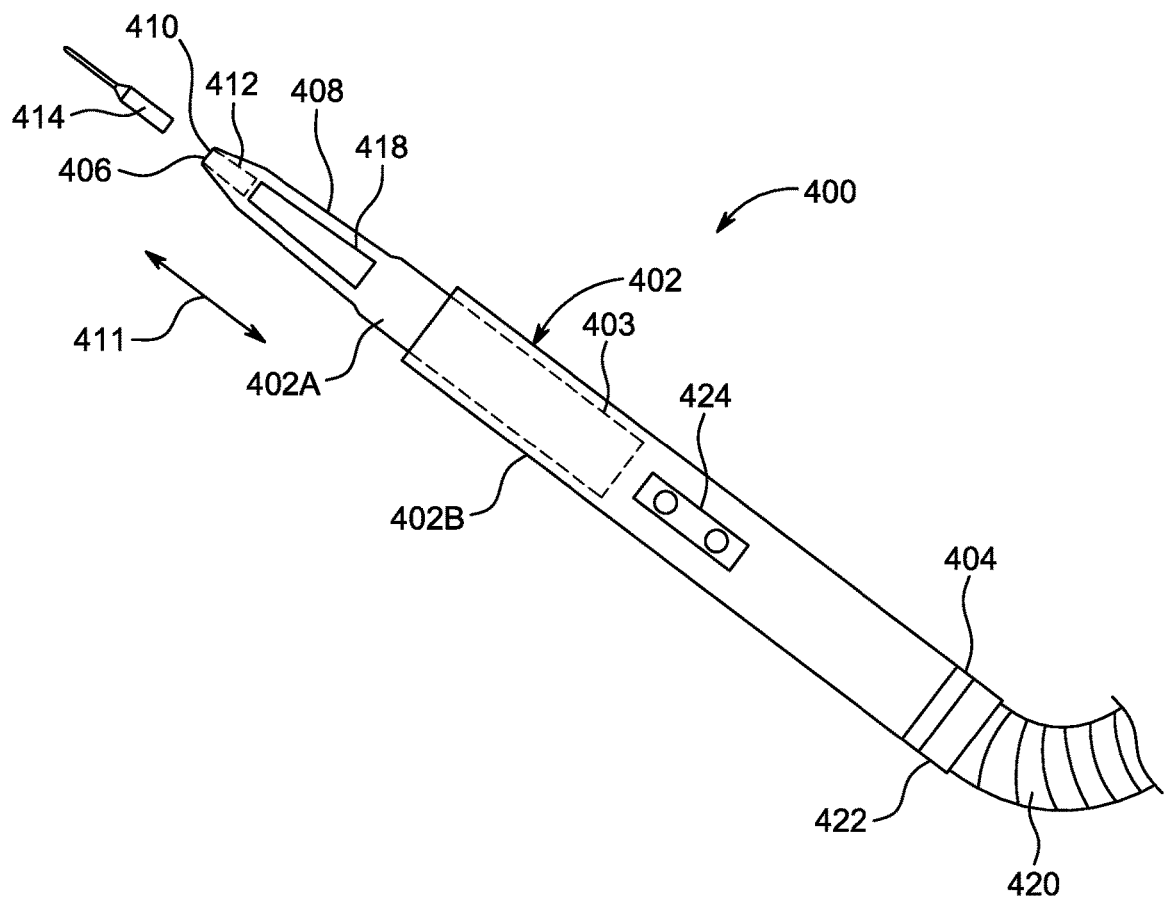
FIG. 11 depicts a side view of a telescoping surgical cauterization tool according to an embodiment of the present disclosure.

Referring now to FIG. 11, there is depicted a hand-held surgical cauterizing device 400 according to an embodiment of the present disclosure. The device 400 may comprise an elongate body member 402. The elongate body member 402 may extend from a proximal end 404 to a distal end 406. The distal end 406 may be preceded by a tapered-distal end portion 408. The tapered-distal end portion 408 may taper in the proximal-to-distal direction and terminate at an apex 410.

The elongate body member 402 may include a first portion 402A and a second portion 402B. The first portion 402A and the second portion 402B may be concentric along a longitudinal axis (not explicitly shown). The first portion 402A may be smaller than the second portion 402B such that the first portion 402A may slide into and out of a hollow passageway formed in the second portion 402B in a telescoping manner as shown by the double arrows indicated by the reference numeral 411. The portion of the first portion 402A within the second portion 402B is indicated by the dashed lines marked with reference numeral 403. Using this feature, a user is able to vary a length of the elongate body member 402 to accommodate different surgical situations.

Formed in the apex 410 may be a slot 412 (shown in dashed lines) configured and adapted for receiving a removable cauterizing tip 414. It will be appreciated that the cauterizing tip 414 may be interchangeable with other tips with different operating characteristics. For example, different parts of a surgical procedure may require different tips.

Formed in the interior of the elongate body member 402 is a hollow passageway (not explicitly shown) that extends forwardly from an outlet in the proximal end 404 to the tapered-distal end portion 408. Formed in the tapered-distal end portion 408 may be at least one smoke intake port 418 that forms a smoke evacuation pathway from an area proximate the tip 414 and into the hollow passageway. A length of the hollow passageway may be varied as the position of the first portion 402A and the second portion 402B of the elongate body member 402 are adjusted with respect to each other.

The outlet of the passageway may be connected to a tube 420 by a connector 422. Electrical leads for powering the tip 414 may be incorporated into the tube 420 or may be separate. In an embodiment, the connector 422 is one of a swivel connector or jointed connector. The tube 420 may be connected to an external suction generation device (not shown, but may be similar to generator 202) to generate a vacuum for removing surgical smoke proximate the tip 414. User controls 424 on the elongate body member 402 may allow a user to energize and de-energize the tip 414. In addition, user controls 424 may allow a user to vary the blend or power to the tip 414. In an embodiment, the device 400 is a monopolar cauterizer.

Figure 12:
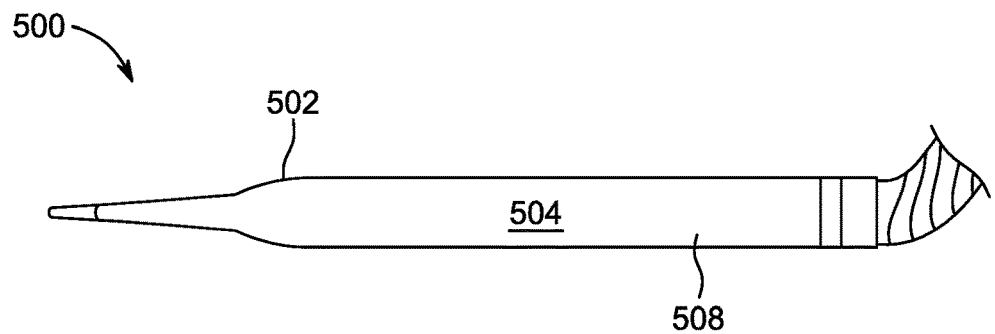
FIG. 12 depicts a side view of a forceps style surgical cauterization tool according to an embodiment of the present disclosure.
Figure 13:
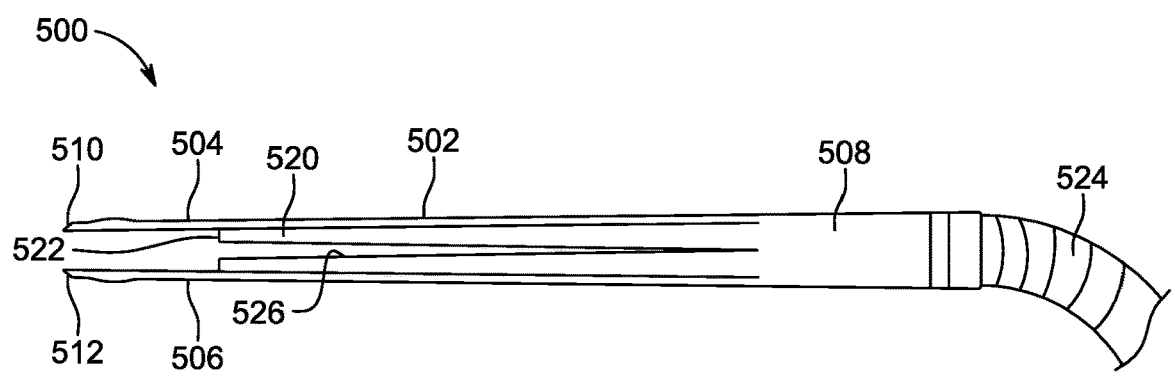
FIG. 13 depicts a top view of the forceps style surgical cauterization tool shown in FIG.

Referring now to FIGS. 12 and 13, there is depicted a hand-held surgical cauterizing device 500 according to an embodiment of the present disclosure. The device 500 may include an elongate body member 502. In an embodiment, the body member 502 comprises a first arm 504 and a second arm 506. The first arm 504 may terminate at a tip 510 and the second arm 506 may terminate at a tip 512. The first arm 504 and the second arm 506 extend from a common base portion 508 on the body member 502 to thereby define forceps. That is, the first arm 504 and the second arm 506 are joined or held fixed at their proximal base ends so as to form a forceps manipulable by a user between an open position and a closed position. It will be appreciated that the forceps may be naturally biased in the open position. The forceps feature may be utilized to grasp tissue during a surgical procedure. The device 500 may operate as one of a monopolar cauterizer and a bipolar cauterizer.

Disposed between the arms 504 and 506 is a smoke evacuation pathway 520 that forms a hollow passage between a smoke evacuation port 522 at the distal end of the pathway 520 and a tube 524. (The tube 524 may be connected to a vacuum or suction generator.)

Figure 13A:
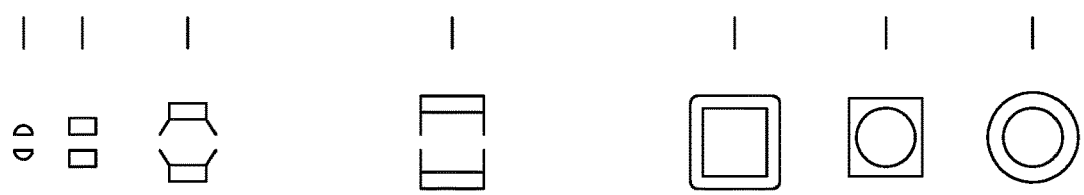
FIG. 13A depicts cross-sectional views of the forceps style surgical cauterization tool shown in FIGS. 12 and 13 with the forceps in the open position.
Figure 13B:
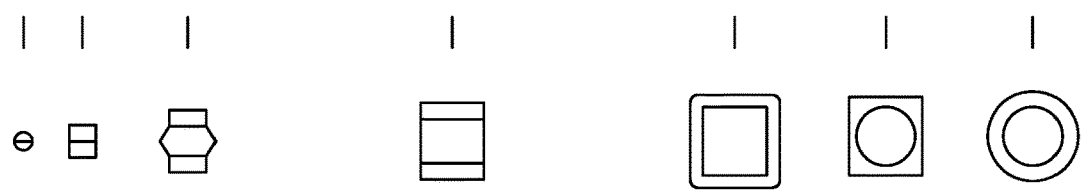
FIG. 13B depicts cross-sectional views of the forceps style surgical cauterization tool shown in FIGS. 12 and 13 with the forceps in the closed position.

The pathway 520 may include a first half having a generally C-shaped cross-section and a second half having a generally C-shaped cross-section such that the pathway 520 may be partially open along its sides as shown by slits 526 when the forceps are in the open position. The slits 526 may close and seal when the forceps are manipulated to the closed position to fully form the smoke evacuation pathway 520. That is, the tips of the generally C-shaped cross-sections may abut against each other to seal the pathway 520 along its sides. FIG. 13A shows cross-sectional views of the elongate body member 502 in relation to FIG. 13 with the forceps in the open position. FIG. 13B shows cross-sectional views of the elongate body member 502 in relation to FIG. 13 with the forceps in the closed position.

Figure 14:
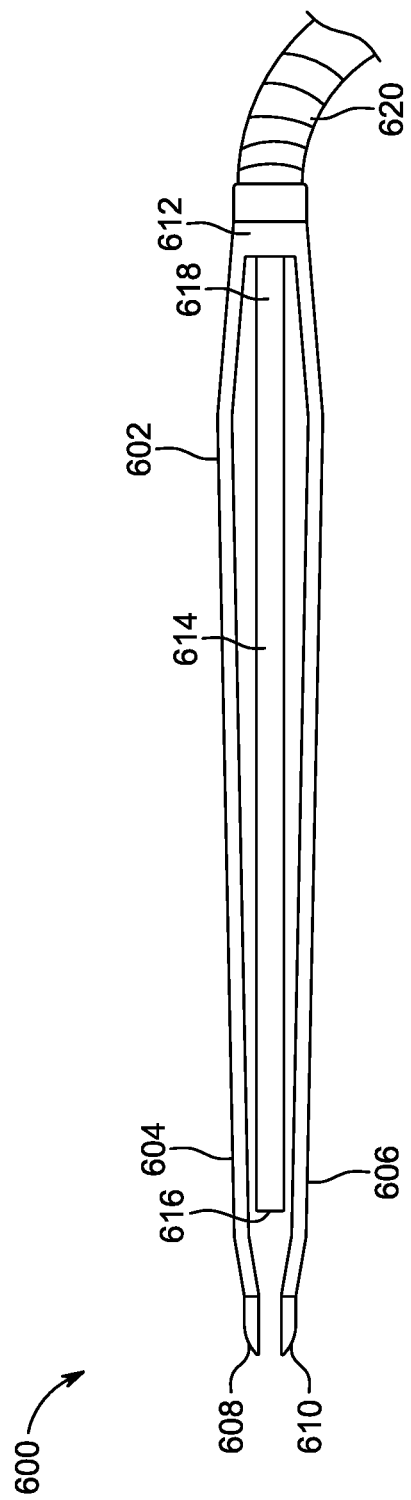
FIG. 14 depicts a side view of a forceps style surgical cauterization tool according to an embodiment of the present disclosure.

Referring now to FIG. 14, there is depicted a hand-held surgical cauterizing device 600 according to an embodiment of the present disclosure. The device 600 may include an elongate body member 602. In an embodiment, the body member 602 comprises a first arm 604 and a second arm 606. The first arm 604 may terminate at a tip 608 and the second arm 606 may terminate at a tip 610. The first arm 604 and the second arm 606 extend from a common base portion 612 to thereby define forceps. That is, the first arm 604 and the second arm 606 are joined or held fixed at their proximal base ends so as to form a forceps manipulable by a user between an open position and a closed position. It will be appreciated that the forceps may be naturally biased in the open position. The forceps feature may be utilized to grasp tissue during a surgical procedure. The device 600 may operate as one of a monopolar cauterizer and a bipolar cauterizer.

Disposed between the arms 604 and 606 is a smoke evacuation member 614 that provides a hollow passageway between a smoke evacuation port 616 at the distal end of the member 614 and an outlet at the proximal end 618 of the member 614. The outlet may be connected to a tube 620. (The tube 620 may be connected to a vacuum or suction generator as described above.) In an embodiment, the smoke evacuation member 614 comprises a tube that extends between the arms 604 and 606. The member 614 may have a small cross-section that does not interfere with the closing of the forceps. In an embodiment, the member 614 is interchangeable with replacement tubes for sterilization or other purposes.

According to an embodiment, the present disclosure provides a disposable or reusable cauterizer that is able to provide enhanced safety from surgical smoke through use of a smoke evacuation feature.

According to an embodiment, the present disclosure provides an apparatus for surgical cauterizing comprising: an elongate body member comprising a tapered distal-end portion terminating at an apex; the elongate body member further comprising an inner sidewall that defines a hollow passageway within an interior of the elongate body member; a cauterizing tip extending from the apex of the elongate body member; at least one smoke intake port formed in the tapered distal-end portion of the elongate body member; and said at least one smoke intake port providing a smoke evacuation pathway between a region proximate the cauterizing tip and the hollow passageway within the elongate body member. According to an embodiment, the hollow passageway exits the elongate body member at an outlet. According to an embodiment, there is further provided a connector for attaching a tube to said outlet. According to an embodiment, the connector is a swivel connector or a jointed connector that allows said tube and the elongate body member to move independently of each other. According to an embodiment, the outlet of the hollow passageway is formed in a proximal end of the elongate body member. According to an embodiment, the at least one smoke intake port comprises one of two intake ports, three intake ports and four intake ports, or more. According to an embodiment, the apparatus further comprises at least one light source positioned on the elongate body member, said at least one light source illuminating an area proximate said cauterizing tip. According to an embodiment, the apparatus further comprises a switch positioned on the elongate body member, said switch operable to activate and deactivate the cauterizing tip. According to an embodiment, the apparatus further comprises a switch positioned on the elongate body member, said switch operable to vary a mode of operation of the cauterizing tip between one of a monopolar cautery, a bipolar cautery, and a thermal cautery. According to an embodiment, the apparatus further comprises a set of cauterizing tips, wherein the cauterizing tip extending from the apex is replaceable by one of the other cauterizing tips in the set.

According to an embodiment, the present disclosure provides an apparatus for surgical cauterizing comprising: a first elongated arm and a second elongated arm, each of said first and second elongated arms having a proximal base end and a distal end; each of the distal ends of the first and second elongated arms having a cauterizing tip extending therefrom; a base connected to each of the first and second elongated arms for joining said first and second elongated arms at their proximal base ends so as to form a forceps manipulable by a user between an open position and a closed position; and wherein each of the first and second elongated arms comprises an inner surface that forms a hollow passageway when the forceps are manipulated to the closed position by a user. According an embodiment, the first and second elongated arms define at least one smoke intake port when the forceps are manipulated to the closed position by a user; and wherein said at least one smoke intake port provides a smoke evacuation pathway from a region proximate the cauterizing tips and into the hollow passageway. According to an embodiment, the hollow passageway exits the surgical cauterizer at an outlet. According to an embodiment, the apparatus further comprises a connector for attaching a tube to said outlet. According to an embodiment, the connector is a swivel connector or a jointed connector that allows said tube and the elongate body member to move independently of each other. According to an embodiment, the apparatus further comprises at least one light source positioned on one of the first and second elongated arms, said at least one light source illuminating an area proximate the cauterizing tips. According to an embodiment, the apparatus further comprises a locking member for locking the forceps in the closed position. According to an embodiment, the apparatus further comprises a switch positioned on the surgical cauterizer that is operable to vary a mode of operation of the cauterizing tips between one of a monopolar cautery, a bipolar cautery, and a thermal cautery. According to an embodiment, the apparatus further comprises a set of cauterizing tips, wherein each of the cauterizing tips on the distal ends of the first and second elongated arms is interchangeable with one of the other cauterizing tips in the set.

According to an embodiment, the present disclosure provides a system for surgical cauterizing comprising: a handheld cauterizing tool comprising: (i) a first elongated arm and a second elongated arm, each of said first and second elongated arms having a proximal base end and a distal end, (ii) each of the distal ends of the first and second elongated arms having a cauterizing tip extending therefrom, (iii) a base connected to each of the first and second elongated arms for joining said first and second elongated arms at their proximal base ends so as to form a forceps manipulable by a user between an open position and a closed position, (iv) wherein each of the first and second elongated arms comprises an inner surface that together form a hollow passageway when the forceps are manipulated to the closed position by a user, (v) wherein the first and second elongated arms define at least one smoke intake port when the forceps are manipulated to the closed position by a user, and (vi) wherein said at least one smoke intake port provides a smoke evacuation pathway from a region proximate the cauterizing tips and through the hollow passageway to an outlet formed in the handheld cauterizing tool; a tube having a first end and a second end, wherein said first end of the tube is connected to the outlet and wherein said second end is connected to an air-suction generating device; and a power supply for energizing one or both of the cauterizing tips. According to an embodiment, the connector is a swivel connector or a jointed connector that allows said tube and the elongate body member to move independently of each other.

According to an embodiment, the present disclosure provides an apparatus for surgical cauterizing comprising a solid or unitary elongate body member comprising a tapered distal-end portion terminating at an apex; the elongate body member further comprising an inner sidewall that defines a hollow passageway within an interior of the elongate body member; a cauterizing tip extending from the apex of the elongate body member; at least one smoke intake port formed in the tapered distal-end portion of the elongate body member; and said at least one smoke intake port providing a smoke evacuation pathway between a region proximate the cauterizing tip and the hollow passageway within the elongate body member.

According to an embodiment, the present disclosure provides an apparatus for surgical cauterizing comprising a solid or unitary elongate body member comprising a tapered distal-end portion terminating at an apex; a cauterizing tip extending from the apex of the elongate body member; the cauterizing tip being removably interchangeable with one or more other cauterizing tips; at least one smoke intake port formed in the tapered distal-end portion of the elongate body member; and said at least one smoke intake port providing a smoke evacuation pathway between a region proximate the cauterizing tip.

According to an embodiment, a surgical cauterizer comprising: a first elongated arm and a second elongated arm, each of said first and second elongated arms having a proximal base end and a distal end; each of the distal ends of the first and second elongated arms having a tip; a base connected to each of the first and second elongated arms for joining said first and second elongated arms at their proximal base ends so as to form a forceps manipulable by a user between an open position and a closed position; and a hollow passageway extending towards the distal ends of the first and second arms, said hollow passageway terminating at a smoke intake port, wherein said hollow passageway is operable to evacuate surgical smoke generated during a surgical procedure from an area proximate the tips of the first and second arms. According to the embodiment, the surgical cauterizer further comprises a tubular member, wherein the hollow passage way is formed in the interior of the tubular member. According to the embodiment, wherein the tubular member is interchangeable with a replacement tubular member. According to the embodiment, wherein each of the first and second arms comprises an inner concave surface, wherein the hollow passageway is formed by the inner concave surfaces of the first and second arms when the first and second arms are manipulated to a closed position. According to the embodiment, wherein each of the first and second arms comprises an inner concave surface, wherein the hollow passageway is formed by the inner concave surfaces of the first and second arms when the first and second arms are manipulated to a closed position.

In the foregoing Detailed Description, various features of the present disclosure are grouped together in a single embodiment for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment. Thus, the following claims are hereby incorporated into this Detailed Description of the Disclosure by this reference, with each claim standing on its own as a separate embodiment of the present disclosure.

It is to be understood that the above-described arrangements are only illustrative of the application of the principles of the present disclosure. Numerous modifications and alternative arrangements may be devised by those skilled in the art without departing from the spirit and scope of the present disclosure and the appended claims are intended to cover such modifications and arrangements. Thus, while the present disclosure has been shown in the drawings and described above with particularity and detail, it will be apparent to those of ordinary skill in the art that numerous modifications, including, but not limited to, variations in size, materials, shape, form, function and manner of operation, assembly and use may be made without departing from the principles and concepts set forth herein.

What is claimed is:

1. An apparatus for surgical cauterizing comprising:
   an elongate body member comprising a first arm and a second arm, each of the first arm and the second arm having a tapered distal-end portion terminating at an apex;
   the elongate body member further comprising a hollow passageway between the first arm and the second arm, wherein the hollow passageway is disposed exteriorly to each of the first arm and the second arm;
   a cauterizing tip extending from the apex of each of the first arm and the second arm;
   a first intake port formed in the tapered distal-end portion of the first arm;
   a second intake port formed in the tapered distal-end portion of the second arm;
   wherein the first intake port and the second intake port are disposed on opposing sides of the elongate body member;
   a third intake port formed between the first arm and the second arm, wherein a perimeter of the third intake port is defined by a first side edge of the first arm and a first side edge of the second arm;
   a fourth intake port formed between the first arm and the second arm, wherein a perimeter of the fourth intake port is defined by a second side edge of the first arm and a second side edge of the second arm;
   wherein the third intake port and the fourth intake port are disposed on opposing sides of the elongate body member;
   wherein the first, second, third and fourth intake ports each taper in a proximal-to-distal direction; and
   said first, second, third and fourth intake ports providing a smoke evacuation pathway between a region proximate the cauterizing tips and the hollow passageway.

2. The apparatus of claim 1, wherein the hollow passageway exits the elongate body member at an outlet.

3. The apparatus of claim 2, further comprising a connector for attaching a tube to said outlet.

4. The apparatus of claim 3, wherein the connector is a swivel connector or a jointed connector.

5. The apparatus of claim 2, wherein the outlet of the hollow passageway is formed in a proximal end of the elongate body member.

6. The apparatus of claim 1, further comprising a switch positioned on the elongate body member, said switch operable to vary a mode of operation between one of a monopolar cautery and a bipolar cautery.

7. The apparatus of claim 1, further comprising a set of cauterizing tips, wherein the cauterizing tip extending from the apex of the first arm is replaceable by one of the other cauterizing tips in the set of cauterizing tips.

* * * * *